US00PP30311P2

(12) United States Plant Patent
Smith

(10) Patent No.: US PP30,311 P2
(45) Date of Patent: Mar. 26, 2019

(54) ***CHRYSANTHEMUM* PLANT NAMED 'CIFZ0061'**

(50) Latin Name: ***Chrysanthemum* x *morifolium***
Varietal Denomination: CIFZ0061

(71) Applicant: SYNGENTA PARTICIPATIONS AG, Basel (CH)

(72) Inventor: Mark A. Smith, Alva, FL (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/932,558

(22) Filed: Mar. 14, 2018

(51) Int. Cl.
*A01H 5/02* (2018.01)

(52) U.S. Cl.
USPC ..... Plt./293
CPC ..... *A01H 5/02* (2013.01)

(58) Field of Classification Search
USPC ..... Plt./293, 290, 287
CPC ..... A01H 5/0255
See application file for complete search history.

*Primary Examiner* — Kent L Bell
(74) *Attorney, Agent, or Firm* — Dale Skalla

(57) ABSTRACT

A new garden type *Chrysanthemum* plant named 'CIFZ0061' particularly distinguished by the medium to large size plant with very round plant habit, a medium sized red-bronze decorative flower color and a natural season response mid to late September.

1 Drawing Sheet

Latin name of the genus and species of the plant claimed: *Chrysanthemum* x *morifolium.*

Varietal denomination: 'CIFZ0061'.

BACKGROUND OF THE NEW PLANT

The present invention comprises a new *Chrysanthemum*, botanically known as *Chrysanthemum* x *morifolium*, and hereinafter referred to by the variety name 'CIFZ0061'.

'CIFZ0061' is a product of a planned breeding program. The new cultivar has medium to large size plant with very round plant habit, a medium sized red-bronze decorative flower color and a natural season response mid to late September 'CIFZ0061' originated from a mutation: Stock x-rayed at 1750 RAD in October of 2013. Single cutting sport from the stock.

The female parent was 'Beverly Bronze', ('CIFZ0032', U.S. Plant Pat. No. 28,319). When compared to the female parent, 'CIFZ0061' has:

1) Similar flower type with smaller size and darker overall color that is more red-bronze/less orange-bronze than the sport parent and less two-tone coloration
2) Blackcloth and natural season response is one or two days faster than sport parent
3) Similar plant habit and overal plant size than the sport parent No male parent.

The first act of asexual reproduction of 'CIFZ0061' was accomplished when vegetative cuttings were propagated from the initial selection, this initial selection took place on Apr. 16, 2014 in Gilroy, Calif.

BRIEF SUMMARY OF INVENTION

Horticultural examination of plants grown from cuttings of the plant initiated in May 2014 in Gilroy, Calif., and continuing thereafter, has demonstrated that the combination of characteristics as herein disclosed for 'CIFZ0061' are firmly fixed and are retained through successive generations of asexual reproduction.

'CIFZ0061' has not been observed under all possible environmental conditions. The phenotype may vary significantly with variations in environment such as temperature, light intensity and day length.

A Plant Breeder's Right for this cultivar has not been applied for. 'CIFZ0061' has not been made publicly available prior to the effective filing date of this application, notwithstanding any disclosure that may have been made less than one year prior to the effective filing date of this application by the inventor or another who obtained 'CIFZ0061' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0061' with colors being as true as possible with an illustration of this type. The photographic drawings show in FIG. 1 a close view of flower of the new variety and in FIG. 2 a flowering plant from an outdoor trial.

Figure 1:
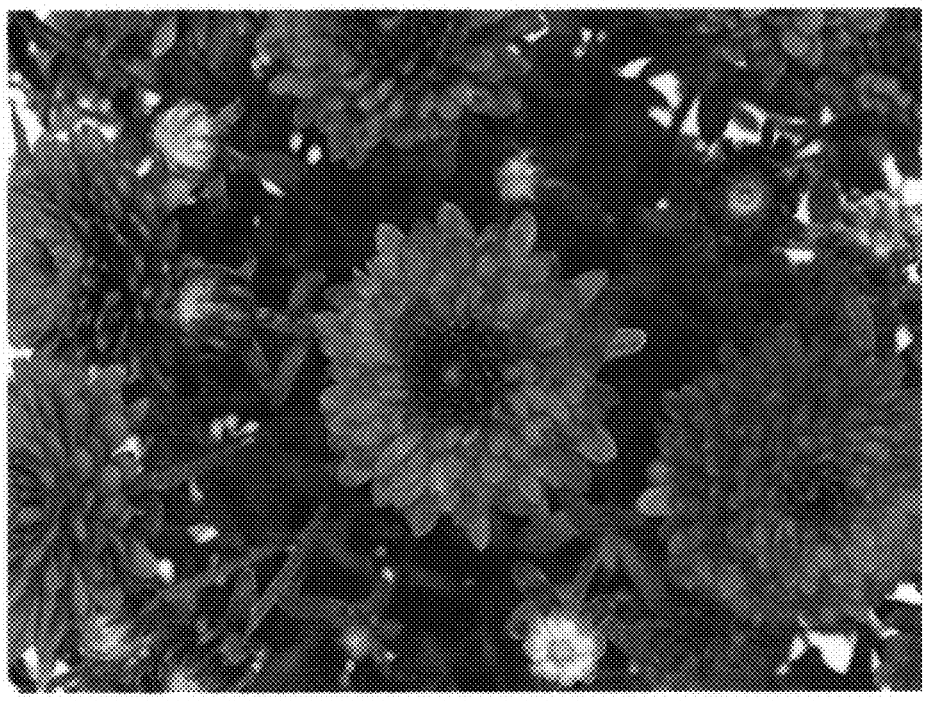
Figure 2:
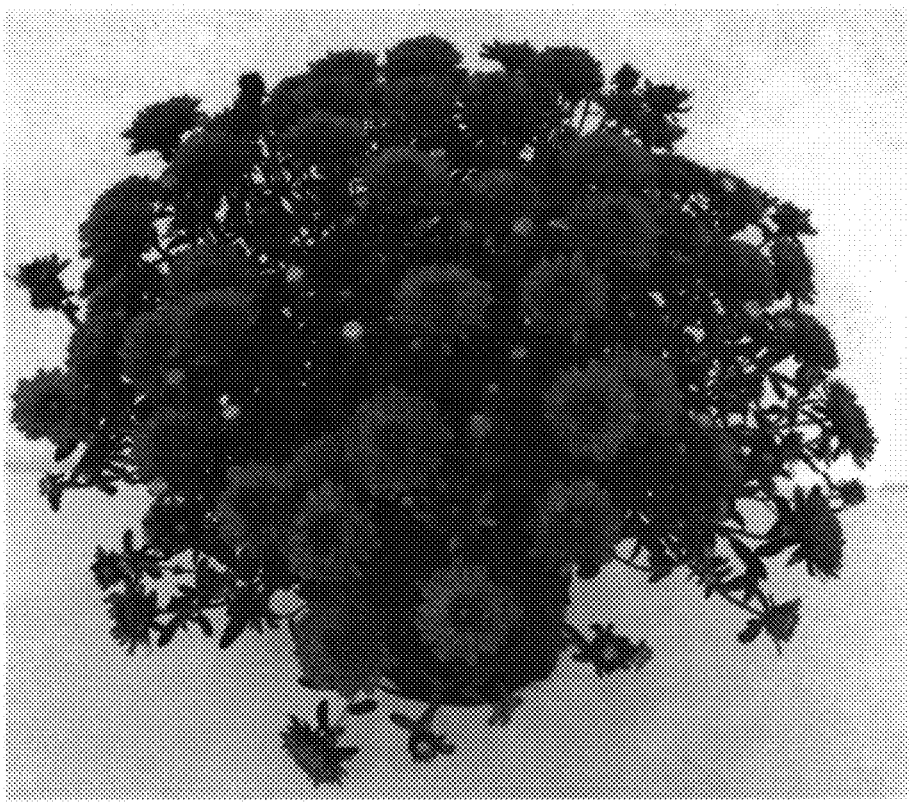

The aforementioned photographs: FIG. 1 and FIG. 2 were taken in August 2017 both showing a plant from the same blackcloth indoor trial in Gilroy, Calif. These plants were about 10 weeks of age. One rooted cutting per pot had been planted in a one gallon pot, not pinched in week 24, and black clothed from week 25. Plants started flowering in August.

DETAILED BOTANICAL DESCRIPTION

The measurements were taken in Gilroy, Calif. in August 2017 on the plants from the aforementioned trial.

Color references are made to The Royal Horticultural Society Colour Chart (R.H.S.) 2001.

TABLE 1

DIFFERENCES BETWEEN THE NEW VARIETY 'CIFZ0061' AND TWO MOST SIMILAR VARIETIES:

| | 'CIFZ0061' | 'Empire Harmony', U.S. Plant Pat. No. 11,830 |
|---|---|---|
| Flowering response (blackcloth): | Similar | Similar |
| Flowering response (natural): | Similar | Similar |
| Flowering: | More uniform | Not very uniform |
| Flower color: | More red-bronze/less orange-bronze color, less two tone coloration | More two-tone coloration, less red/bronze/ more orange bronze coloration |
| Flower size: | Similar | Similar |
| Plants, stems, flexibility: | Stronger plant, less splitting after wind and rain | Weaker plant, more splitting after wind and rain |
| Plant habit or size: | Similar | Similar |

| | 'CIFZ0061' | 'Miora Orange', U.S. Plant Pat. No. 28,155 |
|---|---|---|
| Flowering response (natural): | 6 days faster | 6 days slower |
| Colour fading: | Less fading | More fading |
| Flower color: | More red-bronze/less orange-bronze color, less two tone coloration | More two-tone ration, less red/bronze/more orange bronze coloration |
| Flower size: | Smaller | Bigger |
| Plant habit or size: | Bit wider plant habit | Habit bit more upright |

Plant:

*Form, growth and habit.*—Herbaceous garden-type, stems upright and outwardly spreading, freely branching, strong and moderately vigorous growth habit.

*Plant height (above soil).*—15-20 cm.

*Plant height (inflorescence included).*—16-21 cm.

*Plant width.*—35-39 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B but whiter.

Foliage:

*Arrangement.*—Alternate.

*Immature leaf, color upper surface.*—RHS 137A.

*Immature leaf, color lower surface.*—RHS 137C.

*Mature leaf, color, upper surface.*—RHS 137A.

*Mature leaf, color lower surface.*—RHS 137C.

*Length.*—3.8-4.1 cm.

*Width.*—2.7-3.0 cm.

*Shape.*—Ovate, with distinct lobes.

*Base shape.*—Attenuate.

*Apex shape.*—Mucronate.

*Margin.*—5-lobed (palmate), edge dentate.

*Texture, upper surface.*—Bifid hairs.

*Texture, lower surface.*—Bifid hairs.

*Color of veins, upper surface.*—RHS 138B.

*Color of veins, lower surface.*—RHS 138B.

*Pattern of veining.*—Palmate.

*Petiole color.*—RHS 138A.

*Petiole length.*—1.1-1.7 cm.

*Diameter.*—0.1 cm.

*Texture.*—Covered with bifid hairs.

Stem:

*Quantity of main branches per plant.*—6-8.

*Color of stem.*—RHS 138A.

*Length of stem.*—5.0-7.0 cm.

*Diameter.*—0.4 cm.

*Length of internodes.*—0.4-1.4 cm.

*Texture.*—Bifid hairs.

*Color of peduncle.*—RHS 138A.

*Length of peduncle.*—6.5-7.5 cm.

*Peduncle diameter.*—0.2 cm.

*Texture.*—Bifid hairs.

Inflorescence:

*Type.*—Compositae, solitary, decorative-type inflorescences borne terminally above foliage, ligulate ray florets arranged acropetally on a capitulum giving a double flower.

*Quantity of short days to flowering (response time).*—Approximately 6 weeks.

*Natural season flowering.*—Mid to late September.

*Quantity of inflorescences per plant.*—80-100.

*Lastingness of individual blooms on the plant.*—About six weeks from first color.

*Fragrance.*—Slightly spicy.

Bud (when showing color):

*Color.*—RHS 183A.

*Length.*—0.8-0.9 cm.

*Width.*—1.0-1.1 cm.

*Shape.*—Oblate.

Immature inflorescence:

*Diameter.*—3.0 cm.

*Color of ray florets, upper surface.*—Between RHS 179B and RHS 178C.

*Color of ray florets, lower surface.*—RHS 17A overlain with RHS 2A.

Mature inflorescence:

*Diameter.*—3.7-4.0 cm.

*Depth:* 1.5-1.7 cm.

*Total diameter of disc.*—Very small; not visible as covered by the many rays.

*Receptacle color.*—RHS 144C.

*Receptacle height.*—0.4 cm.

*Receptacle diameter.*—0.4 cm.

Ray florets:

*Average quantity of florets.*—280-320 in several whorls.

*Color of florets, upper surface (abaxial).*—Closest to RHS 181A with RHS 2A at base.

*Color inner surface (adaxial).*—RHS 181A, overlain with RHS 2A at base.

*Length.*—1.0-1.4 cm.

*Width/diameter.*—0.3 cm.

*Shape.*—Elliptical.

*Apex shape.*—Mostly obtuse and dentate.

*Base shape.*—Tube.

*Margin.*—Entire, small incisions may occur at tip.

*Texture, upper surface.*—Papillate.

*Lower surface.*—Papillate.

Disc florets: None present.

Phyllaries:

*Quantity.*—40-50.

*Color, upper surface.*—RHS 137A.

*Color, lower surface*.—RHS 137A.
*Length*.—0.6-0.7 cm.
*Width*.—0.1-0.15 cm.
*Shape*.—Lanceolate.
*Apex shape*.—Acute.
*Base*.—Fused.
*Margins*.—Entire.
*Texture, upper surface*.—Glabrous.
*Texture, lower surface*.—Canescent.

Reproductive organs:

*Pistil*.—One.
*Length*.—0.3-0.6 cm.
*Style color*.—RHS 1C.
*Style length*.—0.3 cm.
*Stigma color*.—RHS 7D.
*Stigma shape*.—Bi-parted.
*Ovary color*.—RHS 145B.
*Ovary length*.—0.15 cm.
*Ovary width*.—0.1 cm.

Androecium:

*Stamens*.—None, as they are usually present in disc florets only, which are not developed.
*Fertility/seed set*.—Has not been determined to date.
*Disease/pest resistance*.—Has not been determined to date.

What is claimed is:

1. A new and distinct variety of *Chrysanthemum* plant named 'CIFZ0061' substantially as illustrated and described herein.

* * * * *